United States Patent [19]
Rhee et al.

[11] Patent Number: 5,752,974
[45] Date of Patent: May 19, 1998

[54] INJECTABLE OR IMPLANTABLE BIOMATERIALS FOR FILLING OR BLOCKING LUMENS AND VOIDS OF THE BODY

[75] Inventors: Woonza M. Rhee, Palo Alto; Richard A. Berg, Los Altos; George H. Chu, Cupertino; Frank A. DeLustro, Belmont; Dan M. Jolivette, Menlo Park, all of Calif.; Kimberly A. McCullough, Kirkland, Wash.

[73] Assignee: Collagen Corporation, Palo Alto, Calif.

[21] Appl. No.: 574,050

[22] Filed: Dec. 18, 1995

[51] Int. Cl.⁶ .................................................. A61B 17/00
[52] U.S. Cl. .................................................. 606/214; 606/1
[58] Field of Search .................................. 606/213, 214, 606/215, 216, 1

[56] References Cited

U.S. PATENT DOCUMENTS

| | | |
|---|---|---|
| 4,963,146 | 10/1990 | Li . |
| 5,019,087 | 5/1991 | Nichols . |
| 5,196,185 | 3/1993 | Silver et al. .................. 424/45 |
| 5,204,382 | 4/1993 | Wallace et al. . |
| 5,213,580 | 5/1993 | Slepian et al. ................ 623/1 |
| 5,443,481 | 8/1995 | Lee .............................. 606/213 |
| 5,456,693 | 10/1995 | Conston et al. ............... 606/192 |
| 5,475,052 | 12/1995 | Rhee et al. .................... 525/54.1 |
| 5,480,644 | 1/1996 | Freed ............................ 424/436 |
| 5,571,181 | 11/1996 | Li ................................. 606/213 |

FOREIGN PATENT DOCUMENTS

| | | |
|---|---|---|
| 0668081 | 8/1995 | European Pat. Off. . |
| 0697218 | 2/1996 | European Pat. Off. . |
| 0713707 | 5/1996 | European Pat. Off. . |
| 0732109 | 9/1996 | European Pat. Off. . |
| WO 94/01483 | 1/1994 | WIPO . |
| WO 403119 | 2/1994 | WIPO . |

OTHER PUBLICATIONS

"Hysteroscopic Approaches for Tubal Closure," John J. Sciarra, *Research Frontiers in Fertility Regulation*, 1980, Chapter 26, pp. 270–286.

Longaker et al. "Maternal Outcome After Open Fetal Surgery: A Review of the First 17 Human Cases", *J. Amer. Med Assoc.*, 265(6):737–741.

*Primary Examiner*—Jeffrey A. Schmidt
*Attorney, Agent, or Firm*—Morrison & Foerster, LLP

[57] ABSTRACT

Methods for completely or partially blocking, augmenting, sealing, or filling various biological lumens and voids within the body of a patient are disclosed. Lumens include arteries, veins, intestines, Fallopian tubes, and trachea. Voids include various lesions, fissures, diverticulae, cysts, fistulae, aneurysms, or other undesirable voids that may exist within a patient's body. In the most general method of the invention, an effective amount of a biomaterial is administered (e.g., via injection, catheter, or surgical implantation) into the lumen or void. Preferred biomaterial compositions for use in the present invention are disclosed.

48 Claims, No Drawings

5,752,974

INJECTABLE OR IMPLANTABLE BIOMATERIALS FOR FILLING OR BLOCKING LUMENS AND VOIDS OF THE BODY

FIELD OF THE INVENTION

This invention is in the field of medical implants and injections. More particularly, it concerns methods for completely or partially blocking, augmenting, sealing, or filling various biological lumens and voids within the body of a patient.

BACKGROUND OF THE INVENTION

Lumens (or lumina) are the spaces in the interior of a tubular structure, such as an artery, vein, intestine, Fallopian tube, trachea, and the like. In some instances, it may be desirable to augment, block, or fill these spaces to effect a preferred biological result. Further, some biological disease states, or treatments for such disease states, cause the formation of undesirable voids within various tissues or organs of the body.

One important lumen structure is the Fallopian tube, which is either of a pair of slender ducts that connect the uterus to the region of each of the ovaries in the female reproductive system. One existing form of birth control is the ligation of both tubes to prevent the movement of eggs or ova into the uterus, thus preventing pregnancy. Unfortunately, this method of birth control requires surgery and is irreversible unless the tubes are cut to remove the ligated portion and the remaining sections of the tubes are reconnected.

As a result of this surgery, the female patient is at greater risk of complications or of failures in the procedure. Further, this type of surgery is expensive and requires hospitalization. Therefore, other methods of birth control, which are less risky and more economical, are preferred.

SUMMARY OF THE INVENTION

The present invention discloses a general method for completely or partially blocking, augmenting, sealing, or filling a biological lumen or void within the body of a patient comprising administering an effective amount of a biomaterial into the lumen or void. A particularly preferred method of the invention comprises administering by injection into the lumen or void an effective amount of a biomaterial composition comprising a biomaterial and a crosslinking agent before substantial crosslinking has occurred between the biomaterial and the crosslinking agent. Another preferred method of the invention comprises injecting an effective amount of a biomaterial composition comprising a particulate dehydrated crosslinked biomaterial and a non-aqueous carrier into the lumen or void. In an alternative method, one or more rods comprising an effective amount of a dehydrated biomaterial composition comprising a crosslinked biomaterial are implanted into the lumen or void.

DETAILED DESCRIPTION OF THE PREFERRED EMBODIMENTS OF THE INVENTION

Preferred Biomaterials for Use in the Invention

Biomaterials for use in the practice of the present invention must be biocompatible, essentially non-immunogenic, and injectable, threadable, or otherwise readily implantable. It is necessary that such biomaterials be in pharmaceutically pure form, or capable of being purified to be in pharmaceutically pure form, such that they can be incorporated into a human body without generating any significant immune response. Biomaterials for use in the invention should be capable of persisting at the site of placement for, preferably, three months or longer; more preferably, six months or longer; most preferably, one to two years or longer. It must be noted that the terms "biomaterial" and "biomaterial composition" are used interchangeably herein and are intended to encompass mixtures of the biomaterials described below.

Preferred biomaterials for use in the practice of the invention include, in general, all biocompatible, naturally occurring or synthetic polymers and, specifically, naturally occurring proteins such as collagen; various synthetic polypeptides such as poly(lysine); polysaccharides such as glycosaminoglycans; proteoglycans; and various polymeric hydrogels.

Proteins such as collagen, fibrin, and elastin are particularly suitable for use in the methods of the present invention. As used herein, the term "collagen" is intended to encompass collagen of any type, from any source, including, but not limited to, collagen extracted from tissue or produced recombinantly, collagen analogs, collagen derivatives, modified collagens, and denatured collagens such as gelatin.

Collagen is the major protein component of bone, cartilage, skin, and connective tissue in animals. Collagen in its native form is typically a rigid, rod-shaped molecule approximately 300 nanometers (nm) long and 1.5 nm in diameter. It is comprised of three collagen polypeptides which form a tight triple helix. The collagen polypeptides are characterized by a long midsection having the repeating sequence —Gly—X—Y—, where X and Y are often proline or hydroxyproline, bounded at each end by the "telopeptide" regions, which constitute less than about 5 percent (%) of the molecule. The telopeptide region of the collagen chains are typically responsible for the crosslinking between chains and for the immunogenicity of the protein.

In general, collagen from any source may be used in the practice of the present invention; for example, collagen may be extracted and purified from human or other mammalian source, such as bovine or porcine corium and human placenta, or may be recombinantly or otherwise produced. The preparation of purified, substantially non-antigenic collagen in solution from bovine skin is basically a three-step process involving solubilization, enzyme treatment, and purification, as described in U.S. Pat. Nos. 4,140,537 and 4,488,911, which are incorporated herein by reference. Commonly owned, allowed U.S. patent application Ser. No. 07/921,810 discloses methods of extracting and purifying collagen from the human placenta. Commonly owned, copending U.S. application Ser. No. 08/183,648 discloses methods of producing recombinant human collagen in the milk of transgenic animals, including transgenic cows. The term "collagen" or "collagen material" as used herein refers to all forms of collagen, including those which have been processed or otherwise modified.

Collagen of any type, including, but not limited to, types I, II, III, IV, or any combination thereof, may be used, although type I is generally preferred. Either atelopeptide or telopeptide-containing collagen may be used; however, when collagen from a xenogeneic source, such as bovine collagen, is used, atelopeptide collagen is generally preferred, because of its reduced immunogenicity compared to telopeptide-containing collagen.

Collagen for use in the present invention may be in the fibrillar or nonfibrillar form. Fibrillar collagen has been shown to have increased persistence in vivo when compared to nonfibrillar collagen. However, the use of nonfibrillar collagen has certain advantages in the practice of the present invention, which will be discussed later in this section. The term "nonfibrillar collagen" as used herein is intended to encompass chemically modified collagens such as succinylated collagen and methylated collagen, both of which can be prepared according to the methods described in U.S. Pat. No. 4,164,559, which is hereby incorporated by reference.

Collagen for use in the practice of the invention may be either crosslinked or noncrosslinked. Noncrosslinked atelopeptide fibrillar collagen is commercially available from Collagen Corporation (Palo Alto, Calif.) at collagen concentrations of 35 mg/ml and 65 mg/ml under the trademarks Zyderm® I Collagen and Zyderm II Collagen, respectively.

Collagen can be crosslinked using methods generally known in the art, such as by heat, radiation, or using conventional chemical crosslinking agents such as, for example, aldehydes, carbodiimides, epoxides, or imidazoles. U.S. Pat. Nos. 4,582,640 and 4,642,117 disclose methods for preparing aldehyde-crosslinked collagens. Glutaraldehyde-crosslinked atelopetpdie fibrillar collagen is commercially available at a collagen concentration of 35 mg/ml from Collagen Corporation under the trademark Zyplast® Collagen Implant.

Noncrosslinked and crosslinked collagens for use in the present invention are generally in aqueous suspension at a concentration between about 20 mg/ml to about 120 mg/ml, preferably, between about 30 mg/ml to about 90 mg/ml.

Denatured collagen, commonly known as gelatin, is also useful in the methods of the invention.

Various synthetically produced polypeptides may also be used in the practice of the invention. As used herein, the term "synthetic polypeptide" is intended to encompass polypeptides that have been produced using recombinant DNA techniques, as well as those produced by other methods of chemical synthesis. Poly(lysine), a synthetically produced polymer of the amino acid lysine (145 MW), is a particularly preferred synthetic polypeptide. Poly(lysine)s have been prepared having anywhere from 6 to about 4,000 primary amino groups, corresponding to molecular weights of about 870 to about 580,000. Poly(lysine)s of varying molecular weights are commercially available from Peninsula Laboratories, Inc. (Belmont, Calif.).

Glycosaminoglycans for use in the present invention include, without limitation, hyaluronic acid, chondroitin sulfate A, chondroitin sulfate C, dermatan sulfate, keratan sulfate, keratosulfate, chitin, chitosan, heparin, and derivatives or mixtures thereof. The preferred concentration of glycosaminoglycan will vary depending upon the specific glycosaminoglycan (or mixture of glycosaminoglycans) that is used.

Proteoglycans, such as decorin, biglycan, and fibromodulin, may also be used in the methods of the present invention. A proteoglycan consists of one or more glycosaminoglycan molecule bound to a core protein. In their native state within the body of an animal, many glycosaminoglycans are generally found in association with core proteins, i.e., in the form of proteoglycans. However, certain glycosaminoglycans, such as hyaluronic acid, are not covalently bound to core proteins, but may be associated with proteoglycans through non-covalent interactions. Hyaluronic acid can also occur by itself, not associated with proteins.

Mixtures of various species of glycosaminoglycans or proteoglycans, various proteins, or mixtures of various glycosaminoglycans or proteoglycans with proteins may be used in the practice of the present invention.

Various polymeric hydrogels can also be used in the methods of the present invention. Commonly owned, copending U.S. application Ser. No. 08/573,799, filed Dec. 18, 1995, (Attorney Docket No. 95-029) discloses a preferred polymeric hydrogel composition comprising a first synthetic polymer crosslinked using a second synthetic polymer, wherein the first synthetic polymer contains two or more nucleophilic groups, and the second synthetic polymer contains two or more electrophilic groups capable of forming covalent bonds with the nucleophilic groups on the first synthetic polymer. The first synthetic polymer preferably contains two or more amino groups or thiol groups and is preferably a synthetic polymer containing two or more lysine residues (such as poly(lysine)); a synthetic polymer containing two or more cysteine residues; or a polyethylene glycol that has been modified to contain two or more amino or thiol groups. The second synthetic polymer is preferably a synthetic hydrophilic or hydrophobic polymer containing two or more succinimidyl groups. In order to form a crosslinked polymer network, the first synthetic polymer preferably contains three or more nucleophilic groups and the second synthetic polymer preferably contains three or more electrophilic groups. Nucleophilic groups on the first synthetic polymer react with electrophilic groups on the second synthetic polymer to form a covalently bound, crosslinked polymer network.

Particularly preferred biomaterial compositions for use in the practice of the invention comprise biomaterials, such as collagen or glycosaminoglycans, crosslinked using synthetic hydrophilic polymers, as disclosed in U.S. Pat. Nos. 5,162,430; 5,324,775; and 5,328,955, the disclosures of which are incorporated herein by reference. Preferred synthetic hydrophilic polymers for use in the invention include functionally activated polyethylene glycols, more preferably, difunctionally activated polyethylene glycols. Particularly preferred difunctionally activated polyethylene glycols are disclosed in U.S. Pat. No. 5,328,955.

As disclosed in commonly owned, allowed U.S. application Ser. No. 08/146,843, glycosaminoglycans must generally be chemically modified by either deacetylation or desulfation (or both) in order to be capable of binding with synthetic hydrophilic polymer molecules. Deacetylation and desulfation can both be effected by the addition of a strong base, such as sodium hydroxide, to the glycosaminoglycan. Deacetylation and/or desulfation provides primary amino groups on the glycosaminoglycan which are capable of covalently binding with functional groups on synthetic hydrophilic polymers such as various polyethylene glycol derivatives. U.S. application Ser. No. 08/146,843 further discloses compositions wherein collagen and one or more species of glycosaminoglycan are crosslinked together using a synthetic hydrophilic polymer to form a heterogeneous conjugate.

A particularly preferred crosslinked biomaterial composition for use in the invention comprises a mixture of particulate crosslinked fibrillar collagen and noncrosslinked fibrillar collagen which is subsequently crosslinked using a synthetic hydrophilic polymer, as disclosed in commonly owned, copending U.S. application Ser. No. 08/344,040. The particulate crosslinked fibrillar collagen is preferably glutaraldehyde-crosslinked fibrillar collagen and preferably comprises between about 25 to about 95 percent, more preferably, between about 60 to about 80 percent by weight, of the final composition. The noncrosslinked fibrillar collagen preferably comprises between about 5 to about 75, more preferably, between about 20 to about 40 percent by weight, of the final composition. The particulate crosslinked fibrillar collagen and noncrosslinked fibrillar collagen are first combined, then crosslinked together using a synthetic hydrophilic polymer, which is preferably a functionally activated polyethylene glycol.

Another preferred biomaterial composition is disclosed in commonly owned, copending U.S. application Ser. No. 08/403,358. This application discloses a biomaterial composition that is crosslinked using a mixture of hydrophilic and hydrophobic crosslinking agents, which may be more resistant to enzymatic or hydrolytic degradation and, as such, display greater in vivo persistence than crosslinked biomaterial compositions prepared using only hydrophilic crosslinking agents. Preferred hydrophobic crosslinking agents include any hydrophobic polymer that contains, or can be chemically derivatized to contain, two or more succinimidyl groups. Commercially available hydrophobic crosslinking agents which contain two or more succinimidyl groups include: disuccinimidyl suberate, bis (sulfosuccinimidyl) suberate, dithiobis (succinimidylpropionate), bis(2-succinimidooxycarbonyloxy)ethyl sulfone, 3,3'-dithiobis (sulfosuccinimidyl)propionate, and their analogs and derivatives. Preferred hydrophilic crosslinking agents include synthetic hydrophilic polymers, particularly functionally activated polyethylene glycol derivatives, as discussed above. As such, the term "crosslinking agent", as used herein, is intended to encompass mixtures of crosslinking agents, such as a mixture of a synthetic hydrophilic polymer and a hydrophobic polymer containing two or more succinimidyl groups.

It is desirable for the biomaterial composition to be hydrophilic in order to allow the biomaterial to hydrate in situ, thereby creating a tight seal or strong adhesion between the collagen composition and the biological component of the body. Such an adhesion to the patient's own tissue will prevent leakage and allow complete blockage of the opening or void that needs to be blocked. The host tissue will also provide ingrowth over time, further strengthening the adhesion of the biomaterial to the tissue.

The hydrophilicity of the crosslinked biomaterial compositions discussed above can be increased by:

(a) using nonfibrillar collagen (particularly, methylated collagen) as the biomaterial, which will require a higher molar ratio of synthetic hydrophilic polymer to collagen in order to achieve optimum crosslinking; or (b) using a higher molecular weight synthetic hydrophilic polymer to crosslink the biomaterial; or (c) crosslinking a mixture of a hydrophilic glycosaminoglycan, such as hyaluronic acid, and collagen together using a synthetic hydrophilic polymer.

As discussed in (b) above, and earlier in the specification, the use of nonfibrillar collagen, preferably methylated collagen, as the biomaterial may be advantageous in the present invention in that methylated collagen requires a higher molar ratio of synthetic hydrophilic polymer to collagen to achieve optimum crosslinking, resulting in a biomaterial composition that is more hydrophilic and will hydrate to a greater degree in situ compared with compositions prepared using fibrillar collagen. Methods of crosslinking chemically derivatized nonfibrillar collagens, including methylated and succinylated collagens, using synthetic hydrophilic polymers are disclosed in commonly owned, allowed U.S. application Ser. No. 08/147,227.

Any of the above crosslinked biomaterial compositions can be dehydrated to form a solid product. As used herein, the term "dehydrated" means that the composition has been dried such that it contains substantially no unbound water. In one preferred embodiment, the biomaterial composition is dehydrated, chopped or cut such that it is present in particulate form, then suspended in a nonaqueous carrier for delivery by injection. The biomaterial composition is preferably extruded in the shape of a thin string before substantial crosslinking has occurred between the biomaterial and the crosslinking agent, allowed to finish crosslinking, then dehydrated. As described in U.S. Pat. No. 5,308,889, the dehydrated crosslinked string is then chopped into small pieces before being suspended in a nonaqueous carrier in preparation for injection to a tissue site.

Alternatively, the biomaterial composition can be extruded into a rod-shaped mold prior to substantial crosslinking, removed from the mold after crosslinking is complete, then dehydrated (or allowed to dehydrate in the mold). One or more of the resulting dehydrated crosslinked biomaterial rods may be implanted in the body of a patient via catheter or using another appropriate method.

Following injection or implantation into the body of a patient, the dehydrated, crosslinked biomaterial compositions prepared as described above will quickly rehydrate to approximately five times their original dehydrated size. The exact amount of swellage will depend upon the hydrophilicity of the composition, which can be increased by varying the biomaterial and/or crosslinking agent as described above.

Biomaterial compositions for use in the present invention may further include one or more biocompatible fluid lubricant, such as, for example, hyaluronic acid, dextran sulfate, dextran, succinylated noncrosslinked collagen, methylated noncrosslinked collagen, glycogen, glycerol, dextrose, maltose, triglycerides of fatty acids (such as corn oil, soybean oil, and sesame oil), and egg yolk phospholipid.

Various particulate materials may also be incorporated into biomaterial compositions for use in the invention. Suitable particulate materials include, without limitation, ceramic particles; particulate crosslinked or non-crosslinked fibrillar collagen; poly(lactic) acid (PLA), poly(glycolic) acid (PGA), and copolymers thereof (PLGA); calcium carbonate; calcium sulfate; gelatin beads; polytetrafluoroethylene beads; silicone rubber beads; beads of various hydrogel polymers (such as polyacrylonitrile-polyacrylamide hydrogels); silicon carbide beads; and glass beads.

U.S. Pat. No. 4,803,075 discloses injectable compositions comprising an aqueous suspension of a particulate biomaterial in a biocompatible fluid lubricant. U.S. Pat. No. 5,352,715 discloses an injectable composition comprising collagen and biocompatible ceramic (preferably, calcium phosphate; most preferably, tricalcium phosphate and/or hydroxyapatite) particles within the size range of 50 to 250 microns present in a pharmaceutically acceptable fluid carrier.

Biomaterial compositions for use in the invention may also incorporate one or more biologically active agent. The term "biologically active agent" or "active agent" as used herein refers to organic molecules which exert biological effects in vivo. Examples of active agents include, without limitation, enzymes, receptor antagonists or agonists, hormones, growth factors, autogenous bone marrow, antibiotics, antimicrobial agents, and antibodies. The term "active agent" is also intended to encompass various cell types which can be incorporated into the compositions of the invention. The term "active agent" is also intended to encompass combinations or mixtures of two or more active agents, as defined above.

Preferred active agents for use in methods of the present invention include growth factors, such as transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are particularly preferred. Members of the TGF supergene family include the beta transforming growth factors (for example, TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB).

Members of the TGF supergene family are multifunctional regulatory proteins. For example, TGF-β2, a 25,000 molecular weight homodimeric peptide, is capable of inducing site-specific healing responses by increasing collagen synthesis and deposition, as well as remodeling at sites of soft tissue repair. TGF-β2 also activates osteoblasts to synthesize collagen in vitro. The most abundant sources of TGF-β2 are bone and platelets.

Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

The type of biologically agent agent used will depend on the particular site and condition to be treated. The amount of biologically active agent to be included in the biomaterial composition will vary depending upon the type, concentration, and amount of biomaterial used; the sex, weight, age, and medical history of the patient; and the particular site and condition being treated. Typically the weight ratio of biologically active agent to biomaterial will be in the range of from about 1:5000 to about 1:50,000.

Antibiotics or antimicrobial agents may be added to the biomaterial composition to reduce the potential for infection at the treatment site. Additionally, local anaesthetics may be used at the injection site to minimize discomfort. Any appropriate additive may be utilized as long as it is compatible with the biomaterial and the particular patient and disease state being treated.

Biologically active agents can be added to the biomaterial during preparation or just prior to treatment. It is preferred, but not required, that the biologically active agents be incorporated into the biomaterial such that the agents are released via a sustained-type delivery. In this way, the agents can be released into the tissue site and surrounding areas and exert their intended therapeutic effects over an extended period of time.

Biologically active agents may be incorporated into the biomaterial composition by admixture. Alternatively, the agents may be covalently linked to the biomaterial using a crosslinking agent such as a functionally activated polyethylene glycol, or affinity bound to the biomaterial using a binding ligand. Processes for covalently binding biologically active agents such as growth factors to collagen using a synthetic hydrophilic polymer, such as a functionally activated polyethylene glycol, are described in commonly assigned U.S. Pat. No. 5,162,430. Processes for affinity binding biologically active agents to collagen via binding ligands such as heparin are disclosed in commonly owned, copending U.S. application Ser. No. 08/405,320, filed Mar. 16, 1995.

Methods of the Invention

The invention provides methods for completely or partially blocking, augmenting, sealing, or filling various lumens or voids within the body of a patient. As used herein, the term "lumen" is intended to encompass various hollow organs or vessels of the body, such as Fallopian tubes, veins, arteries, intestines, trachea, and the like. The term "void" is intended to encompass any hollow space created by congenital abnormalities, disease, aging, and/or surgery, such as extraction of tumors and other growth masses. As such, the term "void" encompasses lesions, fissures, fistulae, cysts, diverticulae, aneurysms, and any other undesirable void present in any tissue or organ of the body which may result from congenital abnormalities, disease, aging, or surgery. For example, the methods of the invention can be used to seal fissures or crevices within a tissue or structure (such as a vessel), or junctures between adjacent tissues or structures, to prevent the leakage of blood or other biological fluids.

According to the most general method of the invention, an effective amount of a biomaterial composition is administered to the site of a lumen or void within the body of a patient. The term "effective amount", as used herein, means the quantity of biomaterial needed to augment, block, or fill the biological structure of interest. The effective amount of biomaterial administered to a particular patient will vary depending upon a number of factors, including: the sex, weight, age, and general health of the patient; the patient's own ability to absorb or break down the biomaterial; the type, concentration, and consistency of the biomaterial; and the particular site and condition being treated. The biomaterial may be administered over a number of treatment sessions.

As described above, an effective amount of one or more biologically active agent, such as a wound healing agent, antibiotic, or antimicrobial agent, can be incorporated into the biomaterial composition. In this context, an "effective amount" refers to the amount of biologically active agent, antibiotic, or antimicrobial agent required to obtain the desired therapeutic effect, such as improved or accelerated healing of the defect or void, or prevention of infection at the site of administration.

As used herein, the term "effective amount", whether in reference to a biomaterial or biologically active agent, also refers to that amount of material which is pharmaceutically and physiologically acceptable to the particular patient undergoing treatment.

In a preferred method of the invention, the biomaterial composition is administered by injection to a lumen or void in need of treatment. In a particularly preferred method of the invention, a biomaterial (including mixtures of different biomaterials) and a crosslinking agent are mixed just prior to injection to the treatment site, then injected before substantial crosslinking has occurred between the biomaterial and the crosslinking agent. This allows the biomaterial composition to continue crosslinking in situ and prevents blockage of the syringe needle with gelled biomaterial. In addition, such in situ crosslinking may allow anchoring of the biomaterial to host tissue by covalently bonding with collagen molecules present within the host tissue. Preferred crosslinking agents for use in the practice of this method are synthetic hydrophilic polymers and mixtures of hydrophilic and hydrophobic crosslinking agents, as described in the previous section.

In an alternative method, crosslinked biomaterial compositions prepared as described in the previous section are molded into a desired shape, such as a rod or string, then dehydrated. The dehydrated biomaterial composition is then implanted into a lumen or void via catheter, endoscope, or other means. Once in contact with biological fluids in the body of the patient, the dehydrated biomaterial rehydrates and swells in size to fill the lumen or void.

In yet another general method, a dehydrated crosslinked biomaterial composition, as described in the previous paragraph, is chopped or cut into small particulates, suspended in a nonaqueous carrier, then injected to fill a lumen or void in need of treatment.

The methods of the invention generally described above are especially useful for a reversible form of birth control or sterility in females, wherein the biomaterial is threaded, injected, or implanted, such that the Fallopian tubes are filled or blocked by the biomaterial, thereby preventing egg and/or sperm from passing through or around the biomaterial. Using this approach, pregnancy would be prevented since the ova or eggs located in the Fallopian tubes would not exit to the uterus and would not make contact with sperm. The blockage, and hence the sterility or birth control, is reversible by removal of the biomaterial or resectioning of the tube after surgery, wherein the blocked portion of the tube is excised and the remaining portions of the tube are reconnected. It is preferable that the sections of the Fallopian tubes blocked with the biomaterial are those directly connected or closest to the uterus.

Administration of the biomaterial for this therapeutic indication can occur via catheter or via endoscopes, such as a fiberoptic scope, hysteroscope, and the like. See "Hysteroscopic Approaches for Tubal Closures," John J. Sciarra, *Research Frontiers in Fertility Regulation*, 1980, Chapter 26, pp. 270–286. Preferably, the biomaterial is injected into the Fallopian tubes using a catheter, such as, for example, the Selective Salpingography Soft Torque™ Catheter, VS™ Recanalization Catheter, or VS™ Falloposcopy Catheter (all from Conceptus, Inc., San Carlos, Calif.).

The delivery of the biomaterial via injection or implantation provides a means to effectively target the biomaterial to a specific site or location, thereby localizing the biomaterial and minimizing systemic side effects. In addition, the biocompatibility of the material minimizes any immunologic reaction of the patient to the biomaterial. Moreover, the administration of the biomaterial via implant or injection is minimally invasive and usually can be performed on an outpatient basis, resulting in a lower cost than other surgical forms of sterility or birth control. The procedure also eliminates patient compliance, since the patient need not follow any specific instructions or remember to ingest or insert other forms of birth control, such as pills, diaphragms, and the like. However, supplemental forms of birth control can be utilized, if desired, especially those which prevent disease transmission.

The biomaterial and the methods of the invention also can be utilized for tracheal occlusions for in utero correction of fetal congenital defects, such as child congenital diaphragmatic hernia (CDH). See Longaker et al., "Maternal Outcomer AFter Open Fetal Surgery: A Review of the First 17 Human Cases", *J. Amer. Med. Assoc.*, 265(6):737–741 (1991). CDH primarily induces pulmonary hypoplasia, thereby lessening the ability of a newborn to adequately exchange oxygen. The condition is typically diagnosed by ultrasound during pregnancy and is caused by the compression of the developing lungs by other internal organs, such as the intestine, stomach, and liver, due to the herniation of the diaphragm. The rapture of the diaphragm allows the internal organs to move into the chest cavity, restricting the development of the lungs, since there is less space for lung growth.

By occluding the fetal trachea, the intrapulmonary pressure gradually increases due to the fluid build-up in the lungs. This pressure increase propels the internal organs slowly from the chest cavity and allows full development of the fetal lungs, preventing pulmonary hypoplasia.

It is desirable that the occlusion method be easily reversible at birth, so that the infant can breathe without difficulty. Fortunately, the umbilical connection between mother and child provides sufficient time to remove the occlusion before the infant must breathe on its own. It is important that the tracheal occlusion method be reproducible, reliable, reversible, and atraumatic, thereby minimizing the risk to the mother and infant both at the time of occlusion and upon removal of the biomaterial, which causes the occlusion. Further, the cell lining of the trachea or the trachea itself must not be severely damaged.

Administration of the biomaterial to the fetal trachea can be via injection, using the ultrasound technique or fiberoptic scope for placement guidance. The biomaterial is placed within the trachea to completely fill it, forming a column of material. Preferably, a suture or stitch is placed through the trachea to hold the biomaterial in place. Since the trachea will expand in size as the fetus matures, it is important to utilize a biomaterial that expands such that the trachea continues to be blocked and the biomaterial is not expelled. Therefore, the preferred biomaterial for this indication will be one that is strongly hydrophilic and can expand at a rate that is equal to the growth rate of the fetal trachea. Methods for increasing the hydrophilicity of a biomaterial composition are described in the previous section.

This method of administration minimizes the surgical risks to the mother and the fetus when compared to other occlusion approaches, such as physically tying off the trachea (see Longaker). It also allows for easy removal, since the biomaterial typically gels and solidifies in situ and can easily be removed with tweezers or similar instruments. This quick and easy removal process lessens the time of non-breathing for the newborn infant. In order to optimize the timing of the birth and to facilitate the biomaterial's removal, the delivery is typically by Caesarean section.

The invention also provides methods for treating undesired lesions, fissures, diverticulae, cysts, fistulae, aneurysms, and any other undesirable void present within the body a patient, by administering a biomaterial to the site of these conditions. For example, the biomaterial can be injected, implanted, or threaded into fistula between viscera or into the opening or orifice from a viscus to the exterior of the patient's body. The biomaterial fills the defect formed by these pathological states and stimulates fibroblast infiltration and healing, resulting in the ingrowth of tissue.

The biomaterial can be introduced by injection through a small gauge needle into one of the fistular orifices, filling all of the branches of the orifice and polymerizing or crosslinking in situ. Alternatively, dehydrated strings or rods of the materials (prepared as previously described) can be threaded into the lesions through an orifice or introduced by catheter. Various types of fistulae can be treated by this method and include anal fistulae, arteriovenous fistulae, bladder fistulae, carotid-cavernous fistulae, external fistulae, gastric fistulae, intestinal fistulae, parietal fistulae, salivary fistulae, vaginal fistulae, anorectal fistulae, and the like.

Diverticulae also can be treated by the methods of the invention. These abnormal physiological structures are pouches or sac openings from a tubular or saccular organ, such as the intestine, the bladder, and the like, and can be filled or augmented by the biomaterial. Cysts, which are abnormal sacs with a membrane lining containing gas, fluid, or semi-solid material, also can be filled, along with pseudocysts, which are an accumulation of fluid in a cyst-like locule, but without an epithelial or other membranous lining. Examples of cysts that can be treated by the invention include serous cysts, sebaceous cysts, dermoid cysts, bone cysts, and the like.

Another method provided by this invention is the administration of a biomaterial to fill in whole, or in part, any void spaces formed as the result of surgical, chemical or biological removal of unnecessary or undesirable growths, fluids, cells, or tissues. The biomaterial can be locally administered at the site of the void, augmenting the remaining and surrounding tissue to aid in the healing process and to minimize infection. This augmentation is especially useful for void sites created after tumor excision, such as after breast cancer surgery, surgery for removal of tumorous connective tissue, bone tissues or cartilage tissue, and the like.

For all the various therapeutic indications that can be treated using the methods of the invention, it is desirable to properly place the biomaterial in the bodily region of interest, such that the biomaterial either is held in place during performance of the method, or held in place for a sufficent length of time to allow polymerization in situ for certain biomaterials. The biomaterial can be localized by the use of a clamp, balloon catheter, umbrella, surgical instrument, and the like. Injection of a biomaterial between a dual balloon catheter can be used to block the lumen anterior and posterior to the catheter tip.

Moreover, there are procedures in which the ultimate removal of the biomaterial is desired or necessary. Therefore, in those procedures, the biomaterial should be exist in a solid or semi-solid form at the time of removal. Removal can occur by physical means, such as surgery, or by mechanical means, such as pressure or suction. The biomaterial also can be pulled from a lumen using strings, wires, and the like, which are firmly embedded or attached to the biomaterial in order to permit complete removal.

An alternative method for removal is the in vivo degradation of the biomaterial, for example, by enzymes such as collagenase. The rate of degradation in vivo and eventual resorption by the body can be controlled by varying a number of factors including, without limitation, the type, concentration, and amount of biomaterial and/or crosslinking agent (if any) used. Higher concentration materials tend to have greater in vivo persistence. Crosslinked biomaterial compositions tend to persist in vivo longer than non-crosslinked formulations; tightly crosslinked biomaterials (ie., those for which the concentration of the particular crosslinking agent employed has been optimized) tend to persist longer than more loosely crosslinked materials.

When functionally activated polyethylene glycols are used as the crosslinking agent, those which incorporate ether linkages may persist longer in vivo than those incorporating ester linkages because of the greater resistance to hydrolysis of the ether linkages. Denatured biomaterials such as gelatin (denatured collagen) generally show the shortest in vivo lifetimes.

EXPERIMENTAL

The following experimental section is offered by of example and not by limitation. The invention is described below in some detail for the purposes of clarity and understanding. It will be apparent, however, that certain changes and modifications may be practiced within the scope of the appended claims.

EXAMPLE 1

(Guinea Pig Bladder Stress Test)

Crosslinked collagen rods were prepared as follows: Fibrillar collagen (65 mg/ml collagen concentration, obtained from Collagen Corporation, Palo Alto, Calif.) was mixed using syringe-to-syringe mixing with difunctionally activated SG-PEG (DSG-PEG, 3800 MW, obtained from Shearwater Polymers, Huntsille, Ala.) in a 1 to 10 molar ratio of collagen to DSG-PEG. The collagen/DSG-PEG reaction mixture was extruded into small diameter (~3 mm inner diameter) tubing. The reaction mixture was incubated in the tubing and allowed to crosslink overnight at 37° C. The tubing was cut in half to dislodge the crosslinked collagen gel in the form of a long thread or rod, which was subsequently air-dried in a flow hood under tension to keep it straight.

A crosslinked collagen rod, prepared as described above, was inserted into each of the ureters of a guinea pig cadaver and cut to size. Approximately 7 cc of water with fluroscein dye was introduced into the bladder via the urethra using a fine gauge needle, then the urethra was ligated beyond the needle insertion point to prevent leakage of the bladder. The filled bladder was viewed under ultraviolet light and it was observed that the crosslinked collagen rod was not dislodged and that the bladder did not leak. The ureter was used as a model for a cell-lined tubular structure, as may be found in a fistula.

EXAMPLE 2

(Fetal Tracheal Occlusion with Crosslinked Collagen for Diaphragmatic Hernia)

Pregnant New Zealand white female rabbits were operated on at day 23 of the gestation period (term is 31 days). With the mother rabbit under general anaesthesis, the uterus was exposed and gestational sacs of individual fetuses identified. A diaphragmatic hernia was created in one fetus through a left thoracotomy by grasping the diaphragm with forceps and cutting it with fine scissors. The fetus was sewn up and returned to the uterus.

A similarly created diaphragmatic hernia was performed on a second fetus; however, this fetus had a tracheal occlusion. Occlusion was performed by a midline dissection of the fetal trachea and injection of a collagen suspension mixed with crosslinking agent through a 25-gauge needle directly into the trachea on the lung side of the dissection. The second fetus was sewn up and returned to the uterus.

A third fetus underwent tracheal occlusion without creation of a diaphragmatic hernia. The remaining fetuses were left to develop in the uterus without surgery.

After operation on the fetuses, the uterus was sewn closed and gestation continued until day 30, at which time the fetuses were sacrificed.

Individual fetal wet lung weight and total body weight was measured, and the fetal wet lung weight to total body weight ratio (LW/BW) was calculated, as shown in Table 1, below.

TABLE 1

Fetal Wet Lung Weight and Total Body Weight

| Animal | Wet Lung Weight (g) | Body Weight (g) | LW/BW |
|---|---|---|---|
| DHTO | 0.566 | 17.246 | 0.0328 |
| DH | 0.238 | 11.580 | 0.0206 |
| NO | 0.271 | 11.868 | 0.0271 |

DHTO = Diaphragmatic Hernia and Tracheal Occlusion with crosslinked collagen
DH = Diaphragmatic Hernia only
NO = No Operation The results presented in Table 1 show that the crosslinked collagen was able to occlude the trachea, resulting in normal lung development in the fetal rabbit.

The disclosures in this application of all articles and references, including patent documents, are incorporated herein by reference.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

The invention has been described above in some detail for the purposes of clarity and understanding. It will be apparent, however, that certain changes and modifications can be practiced within the scope of the appended claims.

What is claimed is:

1. A method for completely or partially blocking, augmenting, sealing, or filling a lumen or void within the body comprising the steps of:
   a) providing a polymer and a hydrophilic crosslinking agent in suspension or solution to form an injectable or implantable biomaterial;
   b) injecting or implanting the biomaterial into a lumen or void within the body; and
   c) allowing the biomaterial to anchor to body tissue surrounding the lumen or void to totally or partially block or fill the lumen or void.

2. The method of claim 1 wherein the polymer is selected from the group consisting of a protein, a synthetic polypeptide, a glycosaminoglycan, a proteoglycan, a polymeric hydrogel, and mixtures thereof.

3. The method of claim 2, wherein the polymer is crosslinked with the crosslinking agent prior to step b), thereby to form a biomaterial which is crosslinked.

4. The method of claim 3, wherein the crosslinked biomaterial is dehydrated prior to step b), and wherein, in step c), the biomaterial rehydrates and swells, thereby allowing the biomaterial to anchor to body tissue surrounding the lumen or void to totally or partially block or fill the lumen or void.

5. The method of claim 4, wherein the dehydrated crosslinked biomaterial is present in particulate form, suspended in a pharmaceutically acceptable nonaqueous carrier, and administered by injection into the lumen or void.

6. The method of claim 4, wherein the dehydrated crosslinked biomaterial is present in rod form and administered into the lumen or void via a catheter or an endoscope.

7. The method of claim 3, wherein the crosslinking agent is selected from the group consisting of aldehydes, carbodiimides, epoxides, and imidazoles.

8. The method of claim 3, wherein the crosslinking agent is a synthetic hydrophilic polymer.

9. The method of claim 8, wherein the synthetic hydrophilic polymer is a functionally activated polyethylene glycol.

10. The method of claim 9, wherein the synthetic hydrophilic polymer is a difunctionally activated polyethylene glycol.

11. The method of claim 2, wherein the polymer is a protein.

12. The method of claim 11, wherein the protein is collagen.

13. The method of claim 12, wherein the collagen is fibrillar collagen.

14. The method of claim 13, wherein the collagen comprises a mixture of particulate crosslinked fibrillar collagen and noncrosslinked fibrillar collagen.

15. The method of claim 14, wherein the particulate crosslinked fibrillar collagen comprises between about 25% to about 95% and the noncrosslinked fibrillar collagen comprises between about 5% to about 75% by weight of the composition.

16. The method of claim 12, wherein the collagen is nonfibrillar collagen.

17. The method of claim 16, wherein the nonfibrillar collagen is methylated collagen.

18. The method of claim 12, wherein the collagen is denatured collagen.

19. The method of claim 2, wherein the polymer is a glycosaminoglycan selected from the group consisting of hyaluronic acid, chondroitin sulfate A, chondroitin sulfate C, dermatan sulfate, keratan sulfate, keratosulfate, chitin, chitosan, heparin, and derivatives thereof.

20. The method of claim 19, wherein the glycosaminoglycan is hyaluronic acid.

21. The method of claim 1, wherein the polymer comprises a crosslinked mixture of collagen and one or more species of glycosaminoglycan.

22. The method of claim 1, wherein the biomaterial further comprises one or more biocompatible fluid lubricant selected from the group consisting of hyaluronic acid, dextran sulfate, dextran, succinylated noncrosslinked collagen, methylated noncrosslinked collagen, glycogen, glycerol, dextrose, maltose, triglycerides of fatty acids, and egg yolk phospholipid.

23. The method of claim 1, wherein the biomaterial further comprises a particulate material selected from the group consisting of ceramic particles, crosslinked or noncrosslinked particulate fibrillar collagen, gelatin beads, polytetrafluoroethylene beads, silicone rubber beads, beads of various hydrogel polymers, silicon carbide beads, glass beads, and mixtures thereof.

24. The method of claim 1, wherein the biomaterial further comprises an effective amount of one or more biologically active agent selected from the group consisting of a wound healing agent, an antibiotic, and an antimicrobial agent.

25. The method of claim 24, wherein the biologically active agent is a wound healing agent selected from the group consisting of: transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives thereof.

26. The method of claim 1, wherein the method further comprises the step of selecting a lumen from the group consisting of a Fallopian tube, a trachea, an artery, a vein, and an intestine prior to step b).

27. The method of claim 1, wherein the method further comprises the step of selecting a void from the group consisting of aneurysms, lesions, fissures, fistulae, cysts, and diverticulae of any organ prior to step b).

28. The method of claim 1, wherein the method further comprises selecting a void caused by a surgical, chemical, or biological removal of growths, fluids, cells, or tissues prior to step b).

29. The method of claim 1, wherein the polymer and the crosslinking agent are administered by injection into the lumen or void before substantial crosslinking has occurred between the polymer and the crosslinking agent, and wherein crosslinking of the polymer and crosslinking agent is completed after administration to the lumen or void, thereby permitting the biomaterial to anchor to body tissue surrounding the lumen or void.

30. The method of claim 1 wherein the polymer and the hydrophilic crosslinking agent are crosslinked after injection or implantation of the biomaterial into the lumen or void, thereby permitting the biomaterial to anchor to body tissue surrounding the lumen or void.

31. The method of claim 1 wherein the polymer is a synthetic polymer.

32. The method of claim 1 wherein the polymer comprises polyethylene glycol.

33. The method of claim 32 wherein the hydrophilic crosslinking agent comprises a functionally activated polyethylene glycol.

34. The method of claim 1 wherein the biomaterial is injected or implanted within a lumen in the body.

35. A method for completely or partially blocking, augmenting, sealing, or filling a biological lumen or void within the body of a patient comprising administering an effective amount of a biomaterial into the lumen or void;
   wherein the biomaterial is crosslinked using a mixture of hydrophilic and hydrophobic crosslinking agents.

36. The method of claim 35, wherein the hydrophilic crosslinking agent is a functionally activated polyethylene glycol.

37. The method of claim 35, wherein the hydrophobic crosslinking agent is a hydrophobic polymer which contains two or more succinimidyl groups prior to bonding with the biomaterial.

38. The method of claim 37, wherein the hydrophobic polymer is selected from the group consisting of: disuccinimidyl suberate, bis(sulfosuccinimidyl) suberate, dithiobis(succinimidylpropionate), bis(2-succinimidooxycarbonyloxy)ethyl sulfone, 3,3'-dithiobis(sulfosuccinimidyl)propionate, and analogs and derivatives thereof.

39. The method of claim 35, wherein the biomaterial is a protein.

40. The method of claim 39, wherein the protein is collagen.

41. The method of claim 40, wherein the collagen is fibrillar collagen.

42. The method of claim 35, wherein the biomaterial comprises a glycosaminoglycan.

43. The method of claim 35, wherein the biomaterial further comprises an effective amount of one or more biologically active agent.

44. The method of claim 35, wherein the method further comprises the step of selecting a lumen from the group consisting of a Fallopian tube, a trachea, an artery, a vein, and an intestine prior to step b).

45. The method of claim 35, wherein the biomaterial and the crosslinking agent are administered by injection into the lumen or void before substantial crosslinking has occurred between the biomaterial and the crosslinking agent.

46. A method for completely or partially blocking, augmenting, sealing, or filling a biological lumen or void within the body of a patient comprising administering an effective amount of a biomaterial into the lumen or void;
   wherein the biomaterial is a polymeric hydrogel which comprises a first synthetic polymer crosslinked using a second synthetic polymer, wherein the first synthetic polymer contains two or more nucleophilic groups, and the second synthetic polymer contains two or more electrophilic groups capable of forming covalent bonds with the nucleophilic groups on the first synthetic polymer.

47. The method of claim 46, wherein the biomaterial comprises collagen.

48. The method of claim 46, wherein the biomaterial further comprises a biologically active agent.

* * * * *